United States Patent
Sang et al.

(10) Patent No.: US 10,519,091 B2
(45) Date of Patent: Dec. 31, 2019

(54) PROCESS FOR PD-CATALYZED HYDROXYCARBONYLATION OF DIISOBUTENE: LIGAND/PD RATIO

(71) Applicant: EVONIK DEGUSSA GMBH, Essen (DE)

(72) Inventors: Rui Sang, Liaocheng (CN); Peter Kucmierczyk, Herne (DE); Kaiwu Dong, Bo Zhou (CN); Ralf Jackstell, Rostock (DE); Matthias Beller, Ostseebad Nienhagen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 16/216,037

(22) Filed: Dec. 11, 2018

(65) Prior Publication Data
US 2019/0194114 A1    Jun. 27, 2019

(30) Foreign Application Priority Data

Dec. 21, 2017 (EP) ..................................... 17209329

(51) Int. Cl.
| | |
|---|---|
| *C07C 51/14* | (2006.01) |
| *C07C 53/00* | (2006.01) |
| *B01J 31/00* | (2006.01) |
| *C07C 51/25* | (2006.01) |
| *B01J 31/22* | (2006.01) |
| *B01J 31/24* | (2006.01) |
| *B01J 31/30* | (2006.01) |
| *C07C 53/128* | (2006.01) |

(52) U.S. Cl.
CPC ......... *C07C 51/252* (2013.01); *B01J 31/2234* (2013.01); *B01J 31/2295* (2013.01); *B01J 31/2409* (2013.01); *B01J 31/30* (2013.01); *C07C 51/14* (2013.01); *B01J 2531/842* (2013.01); *C07C 53/128* (2013.01)

(58) Field of Classification Search
CPC . C07C 51/14; C07C 53/128; B01L 2231/321; B01L 31/2234; B01L 31/2295
See application file for complete search history.

(56) References Cited

U.S. PATENT DOCUMENTS 7,138,544 B2    11/2006    Springer et al.

FOREIGN PATENT DOCUMENTS

EP    1 657 230 A1    5/2006

OTHER PUBLICATIONS

U.S. Appl. No. 16/188,995, Sang et al., filed Nov. 13, 2018.
U.S. Appl. No. 16/189,029, Sang et al., filed Nov. 13, 2018.
U.S. Appl. No. 16/215,991, Sang et al., filed Dec. 11, 2018.
U.S. Appl. No. 16/216,004, Sang et al., filed Dec. 11, 2018.
U.S. Appl. No. 16/216,020, Sang et al., filed Dec. 11, 2018.
U.S. Appl. No. 16/216,053, Sang et al., filed Dec. 11, 2018.
European Search Report dated Jun. 18, 2018 in EP 17 20 9329 (6 pages).
Brennführer, A. et al., Palladium-Catalyzed Carbonylation Reactions of Alkenes and Alkynes. 2009. ChemCatChem. vol. 1. pp. 28-41.

*Primary Examiner* — Sikarl A Witherspoon
(74) *Attorney, Agent, or Firm* — Smith, Gambrell & Russell, LLP

(57) ABSTRACT

Process for Pd-catalyzed hydroxycarbonylation of diisobutene:ligand/Pd ratio.

6 Claims, No Drawings

PROCESS FOR PD-CATALYZED HYDROXYCARBONYLATION OF DIISOBUTENE: LIGAND/PD RATIO

The invention relates to a process for Pd-catalyzed hydroxycarbonylation of diisobutene:ligand/Pd ratio.

Carboxylic acids including propionic acid, adipic acid and fatty acids are used in the preparation of polymers, pharmaceuticals, solvents and food additives. The routes leading to carboxylic acids generally include the oxidation of hydrocarbons, alcohols or aldehydes, the oxidative cleavage of olefins by ozonolysis, the hydrolysis of triglycerides, nitriles, esters or amides, the carboxylation of Grignard or organolithium reagents, and the halogenation and subsequent hydrolysis of methyl ketones in the haloform reaction.

The hydrocarboxylation of olefins is a highly promising and environmentally-friendly method for obtaining carboxylic acids. Acetic acid is produced by carbonylation of methanol, which is carried out with iodide. In the Koch reaction, the addition of water and carbon monoxide to alkenes is catalyzed by strong bases. This method is effective with alkenes that form secondary and tertiary carbocations, e.g. isobutylene to pivalic acid. The hydrocarboxylation occurring with the simultaneous addition of CO and $H_2O$ to alkenesialkynes provides a direct and convenient method for synthesizing carboxylic acids.

The object of the invention was to provide a process affording good conversion in the Pd-catalyzed hydroxycarbonylation of diisobutene (DIBN). This reaction should be carried out in one step.

The object is achieved by a process according to claim 1.

Process comprising the process steps of:
a) addition of diisobutene,
b) addition of a compound comprising Pd, wherein the Pd is capable of forming a complex,
c) addition of the ligand L1:

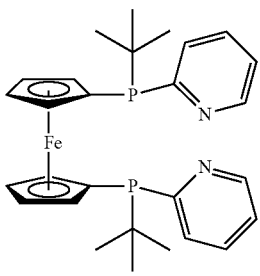

L1 wherein the ligand L1 is added in an amount he range from 1.0 mol to 2.0 mol of ligand per mole of Pd,
d) addition of acetic acid,
e) feeding in CO,
f) heating the reaction mixture such that the diisobutene is converted to the compound P1:

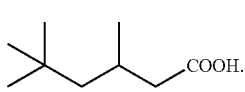

(P1)

In one variant of the process, the compound in process step b) is selected from: $PdCl_2$, $PdBr_2$, $Pd(acac)_2$, $Pd(dba)_2$ (dba=dibenzylideneacetone), $PdCl_2(CH_3CN)_2$.

In one variant of the process, the compound in process step b) is $Pd(acac)_2$.

In one variant of the process, the ligand L1 is added in an amount in the range from 1.25 mol to 1.75 mol of ligand per mole of Pd.

In one variant of the process, the reaction mixture is heated to a temperature in the range from 80° C. to 160° C. in process step f), preferably to a temperature in the range from 100° C. to 140° C.

In one variant of the process, the CO is fed in in process step e) such that the reaction proceeds under a CO pressure in the range from 10 bar to 40 bar, preferably in the range from 10 bar to 30 bar.

In one variant of the process, this process comprises the additional process step g) g) addition of sulfuric acid.

The invention is more particularly elucidated hereinbelow with reference to working examples.

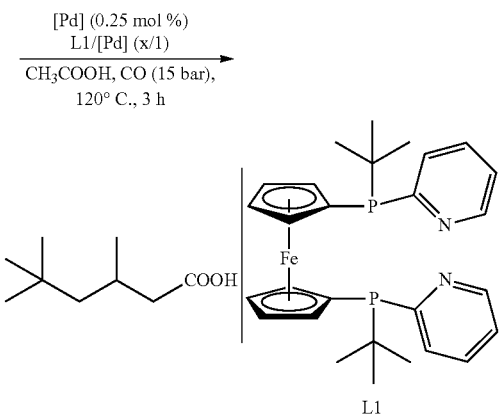

A 4 ml vial was charged with $[Pd(acac)_2]$ (1.75 mg, 0.25 mol %), L1 (4.44 mg, 0.375 mol %), $H_2SO_4$ (3.1 mg, 1.4 mol %) and a stirrer bar that had been dried in an oven. The vial was then sealed with septa (PTFE-coated styrene-butadiene rubber) and a phenol resin cap. The vial was evacuated and refilled with argon three times. $H_2O$ (0.29 ml), acetic acid (0.85 ml) and diisobutene (DIBN) (2.3 mmol) were added to the vial with a syringe. The vial was placed in an alloy plate, which was transferred to an autoclave (300 ml) of the 4560 series from Parr Instruments under argon atmosphere. After flushing the autoclave three times with CO, the CO pressure was increased to 15 bar at room temperature, and subsequently increased to a pressure of 25 bar with $N_2$. The reaction was conducted at 120° C. for 3 h. On conclusion of the reaction, the autoclave was cooled down to room temperature and cautiously decompressed. Isooctane (100 μl) was then added as internal standard. Conversion was measured by GC analysis, The above-described experiment was repeated while varying the L1/Pd ratio. All other parameters were maintained.

The results are compiled in the following table.

| Entry | L1/Pd (mmol/mmol)-L1 (xmol %) | Conversion (%) |
|---|---|---|
| 1* | 1.5/1-0.375 | 92 |
| 2* | 2/1-0.5 | 83 |
| 3 | 3/1-0.75 | 74 |
| 4 | 4/1-1.0 | 69 |

*inventive process

As the experimental results show, the object is achieved by the inventive process.

The invention claimed is:

1. A process for hydrocarbonylation of diisobutene to the corresponding carboxylic acid P1 comprising the process steps of:
   a) adding diisobutene, forming a reaction mixture,
   b) adding a compound comprising Pd, wherein the Pd is capable of forming a complex,
   c) adding ligand L1:

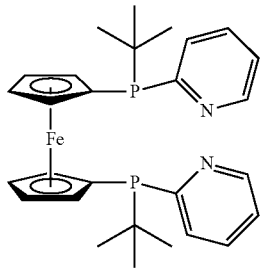

wherein the ligand L1 is added in an amount in the range from 1.25 mol to 2.0 mol of ligand per mole of Pd,
   d) adding acetic acid,
   e) feeding in CO,
   f) heating the reaction mixture such that the diisobutene is converted to the compound P1:

2. The process according to claim 1, wherein the compound in process step b) is selected from: $PdCl_2$, $PdBr_2$, $Pd(acac)_2$, $Pd(dba)_2$ (dba=dibenzylideneacetone), or $PdCl_2(CH_3CN)_2$.

3. The process according to claim 1, wherein the ligand L1 is added in an amount in the range from 1.5 mol to 1.75 mol of ligand per mole of Pd.

4. The process according to claim 1, wherein the reaction mixture is heated to a temperature in the range from 80° C. to 160° C. in process step f).

5. The process according to claim 1, wherein the CO is fed in in process step e) such that the reaction proceeds under a CO pressure in the range from 10 bar to 40 bar.

6. The process according to claim 1, wherein the process comprises the additional process step g):
   g) addition of sulfuric acid.

* * * * *